United States Patent
Nordmann et al.

Patent Number: 5,420,172
Date of Patent: May 30, 1995

[54] CROSS-LINKED EPOXY RESINS HAVING NON-LINEAR OPTICAL PROPERTIES

[75] Inventors: Jens Nordmann, Neunkirchen; Rainer Puehl, Coburg, both of Germany

[73] Assignee: Siemens Aktiengesellschaft, Munich, Germany

[21] Appl. No.: 110,441

[22] Filed: Aug. 23, 1993

[30] Foreign Application Priority Data

Aug. 21, 1992 [DE] Germany ............ 42 27 798.1

[51] Int. Cl.$^6$ .................. C08G 59/02; C08G 59/20
[52] U.S. Cl. ...................... 522/100; 522/170; 525/523; 525/524; 525/526; 525/529; 525/530; 525/531; 525/533; 528/94; 528/99; 528/103; 528/107; 528/109; 528/111; 528/118; 528/120; 528/123; 528/124; 528/327; 528/341; 528/361; 528/365; 528/373; 528/391; 528/393; 528/402; 528/407
[58] Field of Search ............ 528/111, 99, 118, 109, 528/120, 123, 373, 391, 124, 327, 341, 361, 393, 402, 365, 407, 94, 103, 107; 525/523, 533, 524, 526, 529, 530, 531; 522/100, 170

[56] References Cited

FOREIGN PATENT DOCUMENTS

| | | |
|---|---|---|
| 0231770 | 8/1987 | European Pat. Off. |
| 0262680 | 4/1988 | European Pat. Off. |
| 0430143 | 6/1991 | European Pat. Off. |
| 0477667 | 4/1992 | European Pat. Off. |

OTHER PUBLICATIONS

Macromolecules, 1982, vol. 15, pp. 1385–1389, G. R. Meredith et al.: *Optical and Nonlinear Optical Characterization of Molecularly Doped Thermotropic Liquid Crystalline Polymers*.

Appl. Phys. Lett., vol. 49, No. 5, 4 Aug. 1986, K. D. Singer et al.: *Second harmonic generation in poled polymer films*, pp. 248–250.

Electronics Letters, vol. 23, No. 13, 18 Jun. 1987, K. H. Yang et al., pp. 700–701.

Macromolecules, vol. 21, 1988, pp. 2899–2901, American Chemical Society.

J. Opt. Soc. Am. B, vol. 6, No. 4, Apr. 1989, G. T. Boyd: *Applications requirements for nonlinear-optical devices and the status of organic materials*, pp. 685–692.

C. Flytzanis and J. L. Ouder: *Nonlinear Optics: Materials and Devices*, Springer–Verlag (1986), pp. 2–30.

R. A. Hann and D. Bloor: Organic Materials for Nonlinear Optics, The Royal Society of Chemistry (1989), pp. 382–389 and 404–411.

D. S. Chemla and J. Zyss: *Nonlinear Optical properties of Organic Molecules and Crystals*, Academic Press, Inc. (1987), vol. 1, pp. 297–356.

J. Appl. Phys., vol. 66, No. 7, 1 Oct. 1989, Manfred Eich et al.: *Novel second-order nonlinear optical polymers via chemical cross-linking-induced vitrification under electric field*, pp. 3241–3247.

(List continued on next page.)

Primary Examiner—Frederick Krass
Attorney, Agent, or Firm—Kenyon & Kenyon

[57] ABSTRACT

Cross-linked epoxy resins having nonlinear optical properties may be used in nonlinear optical media. These cross-linked epoxy resins may have the following structure:

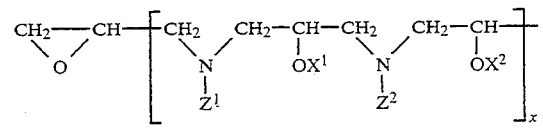

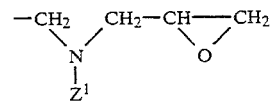

$Z^1$ and $Z^2$ being NLO-chromophores.

17 Claims, No Drawings

OTHER PUBLICATIONS

Appl. Phys. Lett., vol. 56, (1990), pp. 2610-2612, D. Jungbauer et al.: *Highly efficient and stable nonlinear optical polymers via chemical cross-linking under electric field.*

J. Opt. Soc. Am. B, vol. 7, No. 7, Jul. 1990, R. H. Page et al.: *Electrochromic and optical waveguide studies of corona-pooled electro-optic polymer films,* pp. 1239-1250. Macromolecules, vol. 23, (1990), pp. 1891-1894.

"Polymeric Liquid Crystals: Structural Basis for Ferroelectric and Nonlinear Optical Properties", appearing in 6171 Polymers for Advanced Technologies 3 (1992), Aug. No. 5.

"Nonlinear Optical Properties of Organic Materials II", vol. 1147, SPIE, The International Society for Optical Engineering Proceedings, (Aug. 1989).

CROSS-LINKED EPOXY RESINS HAVING NON-LINEAR OPTICAL PROPERTIES

BACKGROUND OF THE INVENTION

The present invention relates to cross-linked epoxy resins and to their production and use.

Non-linear optics is concerned with the interaction between the electromagnetic field of a light wave and a medium in which the light wave is propagated, and with the related creation of new fields having changed properties. If the electromagnetic field interacts with the medium consisting of one molecule or of many molecules, then this field polarizes the molecules.

The polarization which is induced by a local electric field in a molecule can be represented—according to equation (1)—as an exponential series of the electrical field strength:

$$P = \alpha \cdot E + \beta \cdot E^2 + \gamma \cdot E^3 + \ldots \qquad (1)$$

P being the induced polarization and E the induced local electrical field while $\alpha$, $\beta$ and $\gamma$ represent the polarizability of the first, second and third order.

A similar relationship applies on the macroscopic plane—according to equation (2)—for the polarization induced by an external electrical field in a medium consisting of several molecules:

$$P = \epsilon_o(\chi^{(1)} \cdot E + \chi^{(2)} \cdot E^2 + \chi^{(3)} \cdot E^3 + \ldots) \qquad (2)$$

P is in this case again the induced polarization and E the induced local electrical field, $\epsilon_o$ is the dielectric constant, and $\chi^{(1)}$, $\chi^{(2)}$, and $\chi^{(3)}$ represent the dielectric susceptibility of the first, second and third order.

The dielectric susceptibilities of equation (1) have a similar meaning as the molecular coefficients of equation (1): They are material constants which depend on the molecular structure and the frequency and in general also on the temperature. Materials having a dielectric susceptibility of the second order are suitable for frequency doubling: This is is the conversion of light of a frequency $\omega$ into a light of the frequency $2\omega$. Another non-linear optical effect of the second order is the linear electrooptical effect (Pockels-effect); it results from the change in the index of refraction of the optical medium when the electrical field is applied. The optical rectification as well as the sum and difference frequency mixing are further examples of non-linear optical effects of the second order. Fields of use for materials of the above-mentioned type are, for instance, electrooptical switches and areas of information processing and integrated optics, such as optical chip-to-chip connections, wave-guiding in electrooptical layers, Mach-Zehnder-Interferometers and the optical signal processing in sensor technology.

Materials having a dielectric susceptibility of the third order are suitable for frequency tripling of the incident light wave. Further effects of the third order are the optical bistability and phase conjugation. Concrete examples for applications are holographic data processing and purely optical switches for the designing of purely optical computers.

In order to obtain a sufficient non-linear optical effect of the second order, the dielectric susceptibility of the second order $\chi^{(2)}$ must be greater than $10^{-9}$ electrostatic units (esu); this means that the hyperpolarizability $\beta$ must be greater than $10^{-30}$ esu. Another fundamental prerequisite for obtaining a non-linear optical effect of the second order is the non-centrosymmetric orientation of the molecules in the non-linear optical medium; otherwise, we namely have $\chi^{(2)} = 0$. This can be achieved, unless predetermined by the crystal structure, as in the case of crystalline materials, by an orientation of the molecular dipoles. Thus, the highest values of $\chi^{(2)}$ for a non-linear optical medium have been obtained by orientation of the molecular dipoles in electrical fields.

Inorganic materials such as lithium niobate ($LiNbO_3$) and potassium dihydrogen phosphate($KH_2PO_4$), have non-linear optical properties. Semiconductor materials, such as gallium arsenide (GaAs), gallium phosphide (GAP) and indium antimonide (InSb), also have non-linear optical properties. Aside from the advantage of a high electrooptical coefficient of the second order, inorganic materials of the above-mentioned type, however, have some decisive disadvantages. Thus, the processing of these materials is technically very expensive since individual process steps are time-consuming and must be carried out with maximum precision (see in this connection: C. Flytzanis and J. L. Oudar "Nonlinear Optics: Materials and Devices", Springer Publishing Co. (1986), pages 2–30). Such materials are furthermore unsuitable for electrooptical components which operate at high modulation frequencies. Due to the intrinsically present high dielectric constants, there occur namely at high frequencies (above several GHz) such high dielectric losses that working at such frequencies is impossible (see in this connection: "J. Opt. Soc. Am. B", Vol. 6 (1989), pages 685–692).

It is known that organic and polymeric materials with extended $\pi$-electron systems, which are substituted with electron donors and acceptors, can be used in non-linear optical media (see in this connection: R. A. Hann and D. Bloor "Organic Materials for Non-linear Optics", The Royal Society of Chemistry (1989), pages 382–389 and 404–411). Monocrystals on an organic base have a high electrooptical coefficient of the second order and good photochemical stability as compared with $LiNbO_3$. The required high orientation of the non-linear optical molecules is also already present. However, some important criteria speak against industrial utilization of this category of materials. Thus, there is required for producing the monocrystals, both from a solution and from the melt, a period of 14–30 days (see in this connection: D. S. Chemla and J. Zyss "Nonlinear Optical Properties of Organic Molecules and Crystals", Academic Press, Inc. (1987), Vol. 1, pages 297–356). The production process thus does not meet the requirements of industrial production. Additionally, the melting point of the crystals is on the average around 100° C. so that a working temperature range up to 90° C. can probably not be realized. Furthermore, organic crystals cannot be structured and their lateral dimensions are at present still too small to permit designing as an electrooptical component.

Polymeric materials have recently become increasingly important as materials for applications of non-linear optics in the fields of information transmission and integrated optics. These polymeric materials can be produced in the manner that an external electrical field is applied to a specimen which has been heated to above the glass transition temperature; this leads to an orientation of the non-linear optical molecules. After cooling the polymer specimen to below the glass transition temperature, while the electrical field is applied, an anisotropic and thus a non-centrosymmetrical polymer is obtained which has dielectric susceptibilities of the second order.

Non-linear optical compounds which are dissolved in polymers or diffused into polymers can be worked into thin layers as is required for integrated optics (see in this connection: "Macromolecules", Vol. 15 (1982), pages 1385 to 1389; "Appl. Phys. Lett.", Vol. 49 (1986), pages 248 to 250; Electron. Lett.", Vol. 23 (1987), pages 700 to 701). However, the low solubility of the low-molecular compounds, their insufficient distribution in the polymers, the migration of the active molecules out of the polymer matrix and the loss of the non-centrosymmetric orientation of the active molecule species even at room temperature has a disadvantageous effect.

There are also known as non-linear optical compounds polymers having covalently bound non-linear optical molecule components which have at the same time liquid crystal character (see in this connection: EP-OS O 231 770 and EP-OS O 262 680). These materials do not have the above-mentioned disadvantages. However, they are not suitable at the present stage of development for applications in electrical or integrated optics, since in this case optical losses of more than 20 dB/cm result which are caused by the inherent domain scattering. Furthermore, investigations on amorphous non-linear optical polymers have already been reported (see: "Macromolecules, Vol. 21 (1988), pages 2899 to 2901).

Both in the case of liquid crystalline and amorphous polymers with covalently bound non-linear optical molecule units, a much higher concentration of such molecule units can be realized. In this case, a spacer uncouples the molecular mobility of the non-linear optical units from the polymer chain. At the same time, however, the glass transition temperature is drastically reduced. In the case of operating temperatures within the range of the glass transition temperature of the polymers, there must thus be expected the loss of the molecular orientation of the non-linear optical molecule units and the loss of the non-linear optical activity.

SUMMARY OF THE INVENTION

The present invention expands the offering of polymers for non-linear optical media and makes available in this connection in particular polymers which have a high glass transition temperature with simultaneously increased non-linear optical activity which satisfies even high technical requirements.

This is achieved in accordance with the present invention by cross-linked epoxy resins which are obtained from low-molecular epoxy resins having the following structure:

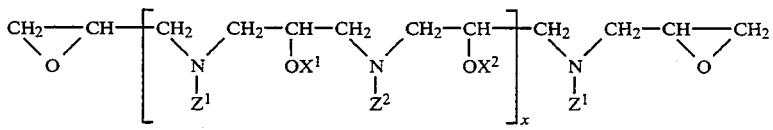

the following applying in this connection:
$x = 1\text{-}20$;
$X^1$ and $X^2 = H$ or $-CO-R-COOH$,
in which connection R is an aliphatic, cyclo-aliphatic, or aromatic grouping;
$Z^1$ and $Z^2$ is in each case a conjugated $\pi$-electron system (E) of the structure $-E-A$ substituted with an electron acceptor (A), the following applying:

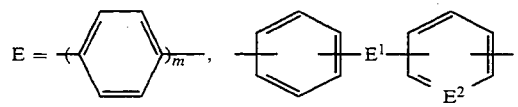

or

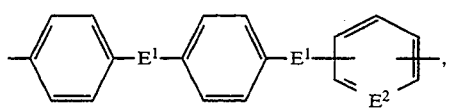

with
$m = 1$ to 3,
$E^1 = -(CH=CH)_n-$, $-N=N-$, $-CH=N-$, $-N=CH-$ or $-C\equiv C-$,
with
$n = 1$ to 3, and
$E^2 = CH$ or $N$;
$A = -NO$, $-NO_2$, $-CN$, $-CF_3$, $-SO_2OR^1$, $-SO_2NR^2_2$,

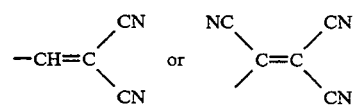

with $R^1$ and $R^2 =$ hydrogen, alkyl, fluoroalkyl alkenyl, aryl or heteroaryl.

The following preferably applies:
$x = 1$ to 10
$X^1 = X^2 = H$ or $-CO-(CH_2)_2-COOH$,
$Z = -E-A$ with $A = -NO_2$ or

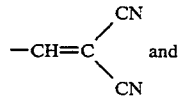

and

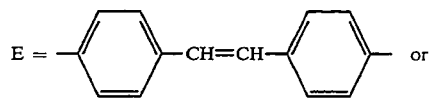

or

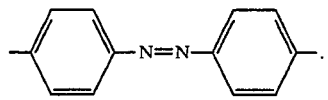

The conjugated $\pi$-electron systems (E) can be substituted on the electron acceptor side-in addition to A- with at least one additional electron acceptor. These substituents should be selected in such a manner that the total of the Hammet constants $\sigma$ of the additional substituents does not exceed the value of the existing substituent (A).

The present invention thus relates to cross-linked epoxy resins of the above-mentioned type. The present invention furthermore relates to the use of such cross-linked epoxy resins in oriented form for non-linear optical media or to non-linear optical polymers in the form of the cross-linked epoxy resins of the above structure.

It has namely surprisingly been found that cross-linked epoxy resins of the above-described type having covalently bound non-linear optical molecular units, on the one hand do not have the above-mentioned disadvantages, but, on the other hand, have the known good polymer-specific properties such as workability into thin layers in the μm range, high concentration of non-linear optical molecule units, low optical attenuation and technically sufficient glass transition temperature. It is furthermore advantageous in the polymers of the present invention that the possibility of a structuring of the non-linear optical polymer layer to form wave guide structures by cross-linking reactions exists, which is not possible in the case of non-cross-linked polymers.

From EP-OS 0 430 143 there are known cross-linked epoxy resins having non-linear optical properties in which the NLO-chromophores can be bound both in the main chain and in the side chain. The low content of ≦10% by weight of NLO-chromophore in the cross-linked product is disadvantageous since larger quantities of an aliphatic and/or aromatic diamine must be used as additional cross-linking agent.

From EP-OS 0 477 667 there are known epoxy resins which contain covalently bound NLO-chromophores and which are used in cross-linked form for non-linear optical media. These epoxy resins are built up from NLO-inactive diglycidyl compounds and NLO-active monoamines. Contrary thereto, NLO-active diglycidyl compounds are used for the building up of the epoxy resins according to the present invention. This has the advantage that in this way a considerable increase in the non-linear optical activity is obtained.

The cross-linked epoxy resins of the present invention are produced in the manner that a glycidyl-functionalized NLO-chromophore of the structure

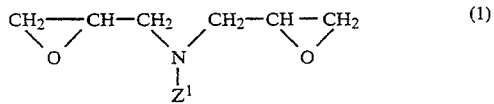

is caused to react with an NLO-chromophore of the structure

in a molar ratio ≧2 and the low molecular epoxy resin obtained in this case is cross-linked. The glycidyl-functionalized NLO-chromophore (1) is preferably 4-(N,N-diglycidylamino)-4'-nitrostilbene or 4-(N,N-diglycidylamino)-4'-nitroazobenzene, the NLO-chromophore (2) is preferably 4-amino4'-nitrostilbene or 4-amino-4'-nitroazobenzene.

For the production of the cross-linked polymers there are thus synthesized from the NLO-chromophores, first of all the epoxy resins which, after having been worked into thin layers having non-linear optical properties in the μm range, are converted into the cross-linked state. Upon the synthesis of the epoxy resins or prior to their cross-linking, NLO-chromophore-unmodified epoxy resins known per se can be added in concentrations between 5 and 7% by weight, preferably between 5 and 25% by weight. In this way, non-linear optical media having a high concentration of non-linear optical molecule units, low optical attenuation and technically sufficient glass transition temperature can be produced. It is also particularly advantageous that the cross-linking of the epoxy resins to form the cross-linked polymers having non-linear optical properties can be carried out prior to, during or after the required orientation of the existing non-linear optical molecule units.

The production of non-linear optical polymers by chemical cross-linking is already known (see: "J. Appl. Phys." Vol. 66 (1989, pages 3241 to 3247). For this purpose there are first of all produced soluble prepolymers by reacting bisphenol A-diglycidyl-ether with 4-nitro-1,2-phenylenediamine which prepolymers are then converted by heating into insoluble cross-linked polymers. In a similar manner, non-linear optical polymers can also be produced from N,N-diglycidyl-4-nitroaniline and N-(2-aminophenyl)-4-nitroaniline (see: "Appl. Phys. Lett.", Vol. 56 (1990), pages 2610 to 2612). From "J. Opt. Soc. Am. B", Vol. 7 (1990), pages 1239 to 1250, there are furthermore known non-cross-linked electro-optical polymer films which are obtained by reacting 4-nitroaniline with bisphenol A-diglycidylether. These polymer materials, however, have the disadvantage that the orientation of non-linear optical molecule units is carried out by corona polarization during the cross-linking of the polymers. As known from experience, no optimal orientation of the molecule units is possible in this way, since the polarization method used leads to a reduced orientation stability of the NLO-units (see in this connection "Macromolecule", Vol. 23 (1990), pages 1891 to 1894).

The production of the epoxy resins in accordance with the present invention as well as the synthesis of the prestages takes place in accordance with methods known per se (see in this connection the illustrative examples). The epoxy resins in which $X^1$ and/or $X^2$ have the meaning —CO—R—COOH, are produced by reacting corresponding compounds having OH-groups with carboxylic acid anhydrides (see in this connection: DD-PS 248 598 and "Makromol. Chem.", Vol. 190 (1989), pages 2673 to 2681). Suitable carboxylic acid anhydrides are in particular succinic acid anhydride, phthalic acid anhydride, tetrahydro-, hexahydro-, methyltetrahydro- and endomethylene tetrahydrophthalic acid anhydride as well as pyromellithic, trimellithic and benzophenone tetracarboxylic acid anhydride.

The cross-linking of the epoxy resins of the present invention can take place either thermally or photochemically. The thermal cross-linking is effected by heating to a temperature which is above the glass transition temperature of the cross-linked final product, i.e. the polymer, preferably about 15° C. above the glass transition temperature. For the thermal cross-linking there can advantageously be added to the epoxy resins imidazol containing initiators as in a concentration between 0.5 and 10% by weight, preferably between 1 and 5% by weight.

The photochemical cross-linking of the epoxy resins is effected by light of a shorter wavelength, preferably by light in the UV-range (290 to 390 nm). In order to initiate the photochemical cross-linking, initiators are added to the reaction mixture which liberate Lewis or Bronsted acids under the influence of light; such compounds are known per se (see for instance "J. Macromol. Sci., Rev. Macromol. Chem," Vol. C21 (1982), pages 187–273). Aryldiazonium, diaryliodonium and triarylsulfonium salts, which have as anion tetrafluoroborate, hexafluorophosphate, hexafluoroarsenate or hexafluoroantimonate, as well as arene iron salts have proven suitable.

In order to improve the surface quality, the workability and/or the compatibility with other polymers, processing adjuvants can be added to the epoxy resins depending on the intended use. Such adjuvants are for instance thixotropic agents, leveling agents, plasticizers, cross-linking agents, lubricants and binders.

The epoxy resins according to the present invention are applied on a substrate in dissolved or liquid form, possibly together with cross-linking-active compounds or initiators, by spin-on deposition, dipping, printing or coating. In this manner, one obtains a non-linear optical arrangement, the epoxy resins being preferably aligned, i.e. oriented in dipolar manner in electrical fields after the cross-linking reaction. There are obtained polymer materials having excellent non-linear optical properties and, due to the cross-linking, increased orientation stability and thus increased storage stability even at higher temperatures of use. These polymers are used in non-linear optical arrangements, in particular in optical components.

DETAILED DESCRIPTION

The present invention will be explained below in greater detail with reference to illustrative examples.

EXAMPLE 1

P Production of N,N-bis(3-chloro-2-hydroxypropyl)-aniline 1.0 mol of aniline and 2.4 mol of epichlorohydrin are heated in 375 ml of ethanol for 16 h under reflux. The solvent is then removed in vacuum and the residue introduced drop by drop into n-hexane. The crystals obtained are filtered off and dried (yield: 75%); MP: 60° C.

EXAMPLE 2

Production of 4-(N,N-Diglycidylamino)-4'-nitroazobenzene 0.25 mol of 4-nitroaniline are stirred in 150 ml of 16% aqueous hydrochloric acid and diazotized at 0° to 5° C. with 0.25 mol of sodium nitrite in 100 ml of water. The diazonium salt solution is filtered, added drop by drop to a solution of 0.25 mol N,N-bis(3-chloro-2-hydroxypropyl)-aniline in 250 ml 5% aqueous hydrochloric acid at 5° to 10° C. and stirred 1 h. The suspension obtained is neutralized with 25% aqueous ammonia solution, 1000 ml of 50% aqueous caustic soda solution are then added drop by drop and stirring takes place for 1 h. The precipitate is drawn off and washed until neutral. The crude product is then dried and chromatographed on silica gel with dichloromethane/tetrahydrofuran as elution agent (yield: 34%); MP: 135°–136° C.

EXAMPLE 3

Production of 4,4'-dinitrostilbene 3.5 mol p-nitrobenzylchloride are dissolved in the hot in 2300 ml of ethanol and a solution of 3.8 mol potassium hydroxide in 1100 ml of aqueous ethanol (70:30) is added thereto drop by drop. After completion of the addition, cooling takes place in an ice bath to 0° C., the precipitate is filtered off and washed in hot water and warm aqueous alcohol (50:50). Drying is then carried out in a vacuum at 75° C. (yield: 83%).

EXAMPLE 4

Production of 4-amino-4'-nitrostilbene 0.34 mol of 4,4'-dinitrostilbene are dissolved in 1800 ml of boiling pyridin. Over a period of 30 min. 540 ml of a 1-molar solution of Na$_2$S/S in water/pyridine (9:1) are added drop by drop to this solution. The mixture is then heated under reflux for 15 min. and 2500 ml of water are then added. After cooling in an ice water bath, the precipitate is filtered off, washed with water and methanol and recrystallized from chlorobenzene (yield: 60%).

EXAMPLE 5

Synthesis of an epoxy resin from 4-(N,N-Diglycidylamino)-4'-nitroazobezene and 4-amino4'-nitrostilbene 8.46 mmol of 4-(N,N-diglycidylamino)-4'-nitroazobenzene and 4.23 mmol 4-amino4'-nitrostilbene are melted together with 0.85 mmol of bisphenol A-diglycidylether at 165° C., homogenized and heated with agitation for two hours at this temperature. The reaction product obtained after cooling, has a glass transition temperature $T_G$ of 99° C. (yield: 100%).

EXAMPLE 6

Hardening of the epoxy resin from 4-(N,N-Diglycidylamino)-4'-nitroazobenzene and 4-amino-4'-nitrostilbene For the hardening, i.e. cross linking, the reaction product of Example 5 is applied, dissolved in a suitable solvent with the addition of 1.5% by weight of an imidazole initiator, to a substrate of glass by spin-on deposition and hardened for three hours at 150° C. The product obtained has a glass transition temperature $T_G$ of 160° C.

EXAMPLE 7

Production of 4-(N,N-Diglycidylamino)-4'-nitrostilbene 0.1 mol of 4-amino-4'-nitrostilbene, 1.0 mol of epichlorohydrin and 0.05 mol of acetic acid are heated for 48 hours at 75° C.; the volatile components are thereupon distilled off in a vacuum. The distillation residue is dissolved in 250 ml of tetrahydrofuran and added drop by drop at 50° C. to 160 ml of a 50% aqueous sodium hydroxide solution. Stirring then takes place for 30 minutes, the solution is cooled and the organic phase separated. The organic phase is then mixed with 1000 ml of water, the precipitate is filtered off, washed until neutral, dried and recrystallized from isopropanol (yield: 70%).

EXAMPLE 8

Synthesis of an epoxy resin from 4-(N,N-Diglycidylamino)-4'-nitrostilbene and 4-amino-4'-nitrostilbene 8.46 mmol of 4-(N,N-diglycidylamino)-4'-nitrostilbene and 4.23 mmol of 4-amino-4'-nitrostilbene are melted together with 0.85 mmol of bisphenol A-diglycidylether at 130° C., homogenized and heated with agitation for 2 h at this temperature. The reaction product obtained after cooling has a glass transition temperature $T_G$ of 73° C. (yield: 100%).

EXAMPLE 9

Hardening of the epoxy resin from 4-(N,N-Diglycidylamino)-4'-nitrostilbene and 4-amino-4'-nitrostilbene For the hardening, i.e. cross-linking, the reaction product of Example 8 is applied, dissolved in a suitable solvent with the addition of 3.0% by weight of an imidazole initiator, to a substrate of glass by spin-on deposition and hardened for 3 h at 150° C. The product obtained has a glass transition temperature $T_G$ of 145° C.

EXAMPLE 10

For the electrooptical examinations, the epoxy resins of the present invention are applied in a suitable solvent and possibly together with cross-linking-active compounds to ITO-coated glass (ITO=indium-tin-oxide) by spin-coating; the layer thickness of the films produced in this manner is customarily 3 to 6 μm. For the electrical polarizing in order to obtain a high non-centro-symanetric orientation, a gold electrode is sputtered onto the film (from the epoxy resin); the counter electrode is in this case the transparent ITO-layer. After heating the sample up into the glass transition temperature range, a dc-voltage is applied, the required increase in voltage being adapted to the orientation behavior of the non-linear optical molecule units in order to avoid electrical breakdowns and thus a destruction of the film. After reaching a polarization field strength of 50 to 100 V/μm, a polarization period of 15 min. is sufficient for orienting the non-linear optical molecule units. The sample is then cross-linked, namely thermally (as in Examples 6 and 9) or photochemically and the sample is then, with the electrical field being constantly applied, cooled to room temperature whereby the orientation is fixed.

The electrooptical examination of the polymer samples takes place by interferometric measurement of an obliquely irradiated laser beam after simple reflection on the gold electrode. The measuring assembly required for this and the evaluation of the measurements are known (see for instance "Appl. Phys. Lett.," Vol. 56 (1990), pages 1734 to 1736). The electrooptical coefficient $r_{33}$ of the polymer of Example 6, which is referred to a polarization field strength of 100 V/μm, amounts to 70 pm/V, while that of the polymer of Example 9, referred to the same polarization field strength, is 60 pm/V.

What is claimed is:

1. Cross-linked epoxy resins produced from epoxy resins having the structure

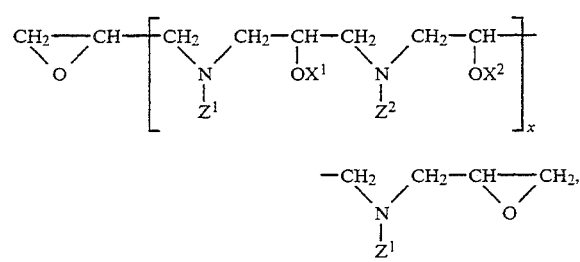

in which connection the following applies:
x=1 to 20;
$X^1$ and $X^2$=H or —CO—R—COOH, R being an aliphatic, cycloaliphatic or aromatic group;
$Z^1$ and $Z^2$ are in each case a conjugated π-electron system (E), substituted with an electron acceptor (A), having the structure —E—A, in which connection the following applies:

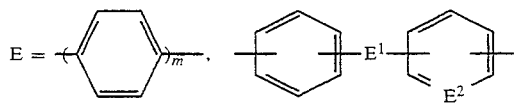

or

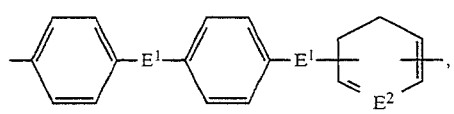

with
m=1 to 3,
$E^1$=—(CH=CH)$_n$—, —N=N—, —CH=N—, —N=CH— or —C≡C—,
with
n=1 to 3, and
$E^2$=CH or N;
A=—NO, —NO$_2$, —CN, —CF$_3$, —SO$_2$OR$^1$, —SO$_2$NR$^2$$_2$,

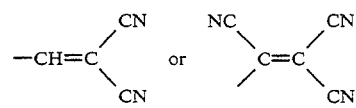

with $R^1$ and $R^2$=hydrogen, alkyl, fluoroalkyl, alkenyl, aryl or heteroaryl.

2. Cross-linked epoxy resins according to claim 1, wherein the following applies:
x=1 to 10,
$X^1$=$X^2$=H or —CO—(CH$_2$)$_2$—COOH,
Z=—E—A with A=—NO$_2$ or

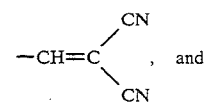, and

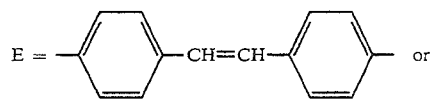 or

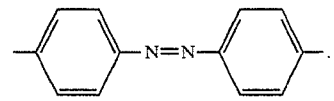.

3. A method for producing the cross-linked epoxy resins of claim 1, wherein a glycidyl-functionalized NLO-chromophore of the structure

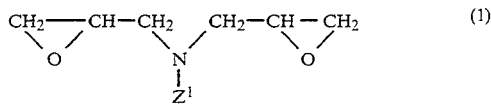 (1)

is caused to react with an NLO-chromophore of the structure

  (2)

in a molar ratio >2 and the epoxy resin obtained in this way is cross-linked.

4. A method according to claim 3, wherein 4-(N,N-Diglycidylamino)-4'-nitrostilbene or 4-(N,N-Diglycidylamino)-4'-nitroazobenzene is used as the glycidyl-functionalized NLO-chromophore of structure (1).

5. A method according to claim 3, wherein 4-amino-4'-nitrostilbene or 4-amino-4'-nitroazobenzene is used as the NLO-chromophore of structure (2).

6. A method according to claim 3, wherein the cross-linking takes place thermally or photochemically.

7. A method according to claim 6, wherein the thermal cross-linking is carried out in the presence of an imidazole compound initiator in a concentration of 0.5 to 10% by weight.

8. A method according to claim 3, wherein NLO-chromophore-free epoxy resins are added in a concentration between 5 and 75% by weight.

9. A method according to claim 8, wherein the concentration of the NLO-chromophore-free epoxy resins amounts to between 5 and 25% by weight.

10. A method for producing the cross-linked epoxy resins of claim 2, wherein a glycidyl-functionalized NLD-chromophore of the structure

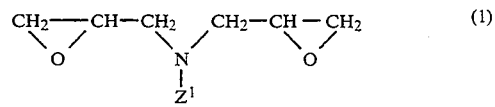  (1)

is caused to react with an NLO-chromophore of the structure

  (2)

in a molar ratio ≧2 and the epoxy resin obtained in this way is cross-linked.

11. A method according to claim 10, wherein 4-(N,N-Diglycidylamino)-4'-nitrostilbene or 4-(N,N-Diglycidylamino)-4'-nitroazobenzene is used as the glycidyl-functionalized NLO-chromophore structure (1).

12. A method according to claim 10, wherein 4-amino-4'-nitrostilbene or 4-amino-4'-nitroazobenzene is used as the NLO-chromophore of structure (2).

13. A method according to claim 10, wherein the cross-linking takes place thermally or photochemically.

14. A method according to claim 13, wherein the thermal cross-linking is carried out in the presence of an imidazole compound initiator in a concentration of 0.5 to 10% by weight.

15. A method according to claim 10, wherein NLO-chromophore-free epoxy resins are added in a concentration between 5 and 75% by weight.

16. A method according to claim 15, wherein the concentration of the NLO-chromophore-free epoxy resins amounts to between 5 and 25% by weight.

17. A non-linear optical medium consisting essentially of a cross-linked epoxy resin according to claim 1 in oriented form.

* * * * *